United States Patent [19]

Luebbe et al.

[11] Patent Number: 4,759,924

[45] Date of Patent: Jul. 26, 1988

[54] COSMETIC STICKS

[75] Inventors: John P. Luebbe, Lawrenceburg, Ind.; James A. Davis, Cincinnati, Ohio

[73] Assignee: The Procter & Gamble Company, Cincinnati, Ohio

[21] Appl. No.: 523,522

[22] Filed: Aug. 16, 1983

Related U.S. Application Data

[63] Continuation-in-part of Ser. No. 426,586, Sep. 29, 1982, abandoned.

[51] Int. Cl.[4] .................. A61K 7/32; A61N 25/18; A61N 25/20
[52] U.S. Cl. .................................. 424/42; 424/65
[58] Field of Search .................. 424/65, DIG. 5, 42

[56] References Cited

U.S. PATENT DOCUMENTS

| | | |
|---|---|---|
| 2,732,327 | 1/1956 | Teller . |
| 2,857,315 | 10/1958 | Teller . |
| 2,900,306 | 8/1959 | Slater . |
| 2,970,083 | 1/1961 | Bell . |
| 3,740,421 | 6/1973 | Schmolka . |
| 3,867,533 | 2/1975 | Schmolka . |
| 4,089,814 | 5/1978 | Schmolka . |
| 4,154,816 | 5/1979 | Roehl et al. . |
| 4,226,889 | 10/1980 | Yuhas . |
| 4,252,789 | 2/1981 | Broad . |
| 4,268,489 | 5/1981 | Gedeon et al. . |

FOREIGN PATENT DOCUMENTS

| | | |
|---|---|---|
| 1042499 | 9/1966 | United Kingdom . |
| 1173743 | 12/1969 | United Kingdom . |
| 1207438 | 6/1970 | United Kingdom . |
| 2020974 | 11/1979 | United Kingdom . |

*Primary Examiner*—Stanley J. Friedman
*Attorney, Agent, or Firm*—Richard C. Witte; John V. Gorman; Douglas C. Mohl

[57] ABSTRACT

Transparent soap gel cosmetic stick compositions comprising a polyhydric aliphatic alcohol, a hydro-alcoholic soluble emollient, water and soap. Such cosmetic sticks possess good cosmetics as well as clarity.

11 Claims, No Drawings

COSMETIC STICKS

CROSS-REFERENCE TO RELATED APPLICATION

This is a continuation-in-part application of our copending application filed Sept. 29, 1982 having Ser. No. 426,586 now abandoned.

TECHNICAL FIELD

The present invention relates to cosmetic compositions in the form of solid sticks. The compositions herein have excellent clarity and may be used for a variety of cosmetic purposes.

BACKGROUND ART

Attempts have been made to realize cosmetic sticks which deliver active ingredients to the skin such as deodorant materials via a vehicle which glides easily over the skin surface and which inparts a cooling sensation to the skin both during and after application. Soap/alcohol gels can provide some of such cosmetic benefits. Examples of such soap gels are disclosed in U.S. Pat. No. 2,732,327, Jan. 24, 1956 to Teller; U.S. Pat. No. 2,857,315, Oct. 21, 1958 to Teller; U.S. Pat. No. 2,900,306, Aug. 18, 1959 to Slater; and U.S. Pat. No. 2,970,083, Jan. 31, 1961 to Bell.

In addition to soap/alcohol sticks, sticks with hydro-alcoholic soluble emollients have been disclosed. References which disclose gels employing such emollients include British Pat. Nos. 1,173,743, Dec. 10, 1969 to Dutton et al; 1,042,499, Sept. 14, 1966 to Shiseido Company; and 1,207,438, Sept. 30, 1970 to Farbwerke Hoechst.

Additional references disclosing soap type sticks include U.S. Pat. Nos. 4,154,816, May 15, 1979 to Roehl, et al; 4,226,889, Oct. 7, 1980 to Yukas; and 4,268,498, May 19, 1981 to Gedeon et al.

While soap gels are old as evidenced by the above patents, such gels either do not possess good clarity and cosmetic properties or require high levels of a short chain, monohydric alcohol. Also, while hydro-alcoholic soluble emollients have been used, products employing them also have problems. It is, therefore, an object of the present invention to provide cosmetic soap gel sticks which are clear, do not require high levels of a short chain, monohydric alcohol, do not present the stinging problems associated with such alcohols and overcome the problems with the prior hydro-alcoholic soluble emollient products.

It is a further object of the present invention to provide cosmetic sticks which have excellent cosmetic properties (e.g. ease of application to skin, "glide", and coolness) and are easy to manufacture.

It is a further object of the present invention to provide such cosmetic sticks which effectively deliver deodorant materials or other cosmetic ingredient to the skin.

It has been surprisingly discovered that the above objectives can be realized by formulating a stick comprising the ingredients described below.

All percentages and ratios used herein are by weight of the total composition unless otherwise designated.

DISCLOSURE OF INVENTION

The present invention relates to cosmetic stick compositions comprising from about 40% to about 70% of a polyhydric aliphatic alcohol, from about 3% to about 10% of a soap, from about 1% to about 20% of a hydro-alcoholic soluble emollient and water. The compositions herein additionally contain less than about 12.5% of a short chain monohydric alcohol (e.g. ethanol, isopropanol, etc.).

POLYHYDRIC ALIPHATIC ALCOHOL

An essential component of the present cosmetic gel stick compositions is a polyhydric aliphatic alcohol containing 2 to 6 carbon atoms, preferably 2 or 3, and from 2 to 6 hydroxyl groups, preferably 2 to 3. The polyhydric aliphatic alcohol component of the stick comprises from about 40% to about 70%, preferably from about 50% to 70%, by weight of the composition.

Suitable polyhydric alcohols for use in the gel compositions herein include ethylene glycol, propylene glycol, trimethylene glycol, glycerine and sorbitol. The most preferred polyol is propylene glycol and mixtures of polyols may be used.

Soap

Another essential component of the compositions herein is a gel forming agent. The gel forming agents used herein are preferably the sodium, potassium and aluminum salts (i.e., soaps) of fatty acids containing from about 14 to 18 carbon atoms.

Soaps generally comprise from about 3% to about 10% by weight, preferably from about 3% to about 8% by weight of the composition. If soap concentrations lower than those specified are employed, the gels formed tend to be dimensionally unstable and tend to deform at summertime temperatures. If concentrations of soap above those specified are utilized, the gels formed tend to be too hard and do not exhibit desirable glide and application characteristics.

The fatty acid portion of the soap gel forming agents should preferably be essentially pure saturated or unsaturated higher fatty acids having a $C_{14}$ to $C_{18}$ backbone. Suitable mixtures of such acids can be employed provided that such mixtures are free from significant proportions of other fatty acids of higher or lower chain length which substantially adversely affect or neutralize the desired gel forming effects.

Examples of fatty acids useful in synthesizing the gel forming agents herein include myristic, palmitic, stearic, oleic, linoleic, linolenic, margaric and mixtures of such acids. Naturally occurring sources of such fatty acids include coconut oil, beef tallow, lanolin, fish oil, beeswax, palm oil, peanut oil, olive oil, cottonseed oil, soybean oil, corn oil, rapeseed oil, rosin acids, and greases. Conventional fractionation and/or hydrolysis techniques can be employed if necessary to obtain the requisite types of fatty acids from such materials.

Preferred fatty acid soap type gel forming agents include sodium stearate, sodium palmitate, potassium stearate, potassium palmitate, sodium myristate and aluminum monostearate. Mixtures of soaps may also be used. The most preferred gel forming agent is sodium stearate.

Hydro-Alcoholic Soluble Emollient

Another essential component of the present composition is hydro-alcoholic soluble emollient having the following formula:

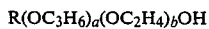
$R(OC_3H_6)_a(OC_2H_4)_bOH$ wherein R is either hydrogen or a hydrocarbon chain having from about 1 to 18 carbon atoms, preferably from about 4 to 16, and $$\frac{a}{a+b} \leq 0.5$$

Preferably a and b are in the range of about 3 to about 26. The hydro-alcoholic soluble emollient is present in the compositions of the present invention at a level of from about 1% to about 20%, preferably from about 1% to about 10% by weight of the composition.

Typical materials meeting the above requirements include PPG-5-Ceteth 20, PPG-3-Myreth-3, PEG-20-Laurate, PEG-6-32 and Polyoxamer 335. All these designations are the designations of the Cosmetic Toiletry and Fragrance Association (CTFA) as set forth in the CTFA Cosmetic Ingredient Dictionary, Second Edition, 1977, incorporated herein by reference. Mixtures of hydro-alcoholic soluble emollients may also be used.

Water

The last essential component of the present compositions is water. Water is generally present at a level of from about 10% to about 40%, preferably from about 14% to about 35%.

Optional Components

The instant stick compositions can contain a variety of optional components suitable for improving compositions efficacy, stability, cosmetics and/or aesthetics. Such optional components include deodorant materials, non-water soluble emollients, perfumes, dyes, pigments, coloring agents and the like.

A preferred optional ingredient of the instant compositions is a conventional deodorant material. Suitable deodorants include bacteriostatic quaternary ammonium compounds such as cetyltrimethylammonium bromide, cetyl pyridinium chloride, benzethonium chloride, diisobutyl phenoxy ethoxy ethyl dimethyl benzyl ammonium chloride, N-alkylpyridinium chloride, N-cetyl pyridinium bromide, sodium N-lauroyl sarcosine, sodium N-palmetoyl sarcosine, lauroyl sarcosine, N-hyristoyl glycine, potassium N-lauroyl sarcosine and stearyl trimethyl ammonium chloride. Another deodorant material useful in the present compositions is 2-4-4'-trichloro 2'hydroxydiphenyl ether, Triclosan. If present, deodorants generally comprise from about 0.1% to 1.0% by weight of the composition, but may comprise up to 20% when a material such as sodium aluminum chlorhydroxy lactate is used.

Another preferred optional component of the instant compositions is a non-water soluble emollient. Materials of this type include fatty esters, fatty ethers, alkoxylated fatty esters, fatty alcohols and low molecular weight silicone fluids. Typical materials include isopropyl palmitate, myreth-4, PEG-8-distearate, cetyl alcohol, dimethicone copolyol, cyclomethicone and dimethicone. The non-water soluble emollient, if present, comprises up to 10%, preferably about 1% to about 5%, of the total composition. A short chain monohydric alcohol (e.g. ethanol) may also be used in the present compositions provided it is present at a level of 12.5% or less.

Other optional ingredients such as perfumes, dyes, pigments, coloring agents and the like, if present, comprise from about 0.1% to 1.5% by weight of the compositions. Acceptable dyes or coloring agents include FD&C Blue #1 and FD&C yellow #5.

Method of Manufacture

The gel sticks of the present invention are made by combining the ingredients in liquid form and pouring the mixture into a form having the desired shape. The solid materials are melted using a temperature of about 180° F. to 200° F.

Composition Use

The gel sticks herein are used by the consumer by rubbing the stick on the area of the body where application is desired. In the case of a deodorant stick the stick is rubbed in the axilla area to apply the deodorant agent.

The following examples further describe and demonstrate preferred embodiments within the scope of the present invention. The examples are given solely for the purpose of illustration and are not to be construed as limitations of this invention. Many variations thereof are possible without departing from the invention's spirit and scope.

EXAMPLE I

Given below is an example of the compositions of the present invention.

| Component | % |
|---|---|
| Water | 29.7 |
| Propylene Glycol | 56.8 |
| PPG-3 Myristyl Ether | 2.5 |
| PPG-5-Ceteth-20 | 3.0 |
| Sodium Stearate | 6.8 |
| Triclosan | 0.3 |
| Color | 0.1 |
| Fragrance | 0.8 |
| | 100.0 |

The composition is clear and possesses good cosmetic properties.

EXAMPLE II

Given below is another example of the present invention.

| Component | % |
|---|---|
| Water | 29.7 |
| Propylene Glycol | 56.8 |
| PPG-3 Myristyl Ether | 2.5 |
| PPG-3-Myreth-3 | 3.0 |
| Sodium Stearate | 6.8 |
| Triclosan | 0.3 |
| Color | 0.1 |
| Fragrance | 0.8 |
| | 100.0 |

This composition possesses properties similar to those of the Example I composition.

EXAMPLE III

A third composition of the present invention is shown below.

| Component | % |
|---|---|
| Water | 29.7 |
| Propylene Glycol | 56.8 |
| PPG-5-Ceteth-20 | 3.0 |
| Sodium Stearate | 6.8 |
| Triclosan | 0.3 |
| Color | 0.1 |

-continued

| Component | % |
|---|---|
| Fragrance | 0.8 |
| PPG-14 Butyl Ether | 2.5 |
| | 100.0 |

This composition is also clear and possesses good cosmetics.

EXAMPLE IV

Another composition of the present invention is shown below.

| Component | % |
|---|---|
| Water | 32.2 |
| Propylene Glycol | 56.8 |
| PPG-5-Ceteth-20 | 3.0 |
| Sodium Stearate | 6.8 |
| Triclosan | 0.3 |
| Color | 0.1 |
| Fragrance | 0.8 |
| | 100.0 |

This composition is clear and possesses good cosmetics.

EXAMPLE V

Another composition of the present invention is shown below.

| Component | % |
|---|---|
| Water | 29.7 |
| Glycerine | 56.8 |
| PPG-3 Myristyl Ether | 2.5 |
| PPG-5-Ceteth-20 | 3.0 |
| Sodium Stearate | 6.8 |
| Triclosan | 0.3 |
| Color | 0.1 |
| Fragrance | 0.8 |
| | 100.0 |

This composition is clear and possesses good cosmetics.

EXAMPLE VI

Below is given another composition of the present invention.

| Component | % |
|---|---|
| Propylene Glycol | 61.7 |
| PPG-5-Ceteth 20 | 3.2 |
| PPG-3 Myristyl Ether | 1.7 |
| Perfume | 1.0 |
| Irgasan | 0.3 |
| Color | 0.4 |
| Water | 27.7 |
| Sodium Stearate | 4.0 |
| | 100.0% |

This composition is clear and possesses good cosmetics.

EXAMPLE VII

A further example of the present invention is:

| Component | % |
|---|---|
| Propylene Glycol | 61.7 |
| PPG-5 Ceteth 20 | 3.2 |
| PPG-3 Myristyl Ether | 1.7 |
| Perfume | 1.0 |
| Irgasan | 0.3 |
| Color | 0.4 |
| Water | 26.7 |
| Sodium Stearate | 2.0 |
| Al. Mono Stearate | 3.0 |
| | 100.0% |

EXAMPLE VIII

A further example of the present invention is:

| Component | % |
|---|---|
| Propylene Glycol | 62.00 |
| PPG-5-Ceteth 20 | 2.00 |
| PPG-3 Myristyl Ether | 1.75 |
| Perfume | 1.00 |
| Irgasan | 0.30 |
| Color | 0.35 |
| Water | 19.05 |
| SDA-40 | 9.75 |
| Sodium Stearate | 3.80 |
| | 100.0% |

EXAMPLE IX

A further example of the present invention is:

| Component | % |
|---|---|
| Propylene Glycol | 62.00 |
| PPG-5-Ceteth 20 | 2.00 |
| PPG-3 Myristyl Ether | 1.75 |
| Perfume | 1.00 |
| Irgasan | 0.30 |
| Color | 0.35 |
| Water | 17.80 |
| SDA-40 | 11.00 |
| Sodium Stearate | 3.80 |
| | 100.00% |

This composition is clear and possesses good cosmetics.

What is claimed is:

1. A clear, cosmetic gel stick composition consisting essentially of:
   a. from about 40% to about 70% of an aliphatic, polyhydric alcohol having from 2 to 6 carbon atoms and from 2 to 6 hydroxyl groups;
   b. from about 3% to about 10% of a soap;
   c. from about 1% to about 20% of a hydro-alcoholic soluble emollient having the formula $$R(OC_3H_6)_a(OC_2H_4)_bOH$$

wherein R is selected from the group consisting of hydrogen and hydrocarbon chains having from about 1 to about 18 carbon atoms and $\frac{a}{a+b}$ is $\leq 0.5$;

and
   d. from about 10% to about 40% water; wherein said composition contains less than about 12.5% of a short chain, monohydric alcohol.

2. A stick composition according to claim 1 wherein the level of soap is from about 3% to about 8%, the level of the hydro-alcoholic soluble emollient is from about 1% to about 10% and the level of water is from about 14% to about 35%.

3. A stick composition according to claim 2 wherein the soap is selected from the group consisting of a sodium salt, a potassium salt or an aluminum salt of a fatty acid containing from about 14 to about 18 carbon atoms and mixtures thereof and R in the condensation product is a hydrocarbon chain having from about 4 to about 16 carbon atoms.

4. A stick composition according to claim 3 which in addition contains a deodorant material.

5. A stick composition according to claim 3 which in addition contains up to about 10% of a non-water soluble emollient.

6. A stick composition according to claim 5 wherein the polyhydric alcohol is selected from the group consisting of ethylene glycol, propylene glycol, trimethylene glycol, glycerine, sorbitol and mixtures thereof.

7. A stick composition according to claim 6 wherein the soap is selected from the group consisting of sodium stearate, sodium palmitate, sodium myristate, potassium stearate, potassium palmitate, aluminum monostearate and mixtures thereof.

8. A stick composition according to claim 7 wherein the hydro-alcoholic soluble emollient is selected from the group consisting of PEG-5-Ceteth-20, PPG-3-Myreth-3, PEG-20-Laurate, PEG-6-32, Polyoxamer 335 and mixtures thereof.

9. A stick composition according to claim 8 wherein the polyhydric alcohol is propylene glycol.

10. A stick composition according to claim 9 wherein the soap is sodium stearate.

11. A stick composition according to claim 10 wherein the hydro-alcoholic soluble emollient is PPG-5-Ceteth-20.

* * * * *